(12) United States Patent
Liu

(10) Patent No.: US 11,324,972 B2
(45) Date of Patent: May 10, 2022

(54) RADIOTHERAPEUTIC DEVICE AND LASER VERIFICATION APPARATUS THEREOF

(71) Applicant: OUR NEW MEDICAL TECHNOLOGIES, Shenzhen (CN)

(72) Inventor: Haifeng Liu, Xi'an (CN)

(73) Assignee: OUR NEW MEDICAL TECHNOLOGIES, Shenzhen (CN)

( * ) Notice: Subject to any disclaimer, the term of this patent is extended or adjusted under 35 U.S.C. 154(b) by 641 days.

(21) Appl. No.: 15/527,386

(22) PCT Filed: Nov. 21, 2014

(86) PCT No.: PCT/CN2014/091843
§ 371 (c)(1),
(2) Date: May 17, 2017

(87) PCT Pub. No.: WO2015/096572
PCT Pub. Date: Jul. 2, 2015

(65) Prior Publication Data
US 2020/0222726 A1 Jul. 16, 2020

(30) Foreign Application Priority Data
Dec. 25, 2013 (CN) .......................... 201320862151.9

(51) Int. Cl.
*A61N 5/00* (2006.01)
*A61N 5/10* (2006.01)
(Continued)

(52) U.S. Cl.
CPC .............. *A61N 5/1077* (2013.01); *A61N 5/06* (2013.01); *A61N 5/067* (2021.08); *A61N 5/1084* (2013.01);
(Continued)

(58) Field of Classification Search
CPC ...... A61N 2005/067; A61N 2005/1094; A61N 2005/1095; A61N 5/1077; A61N 5/06; A61N 5/1084
See application file for complete search history.

(56) References Cited

U.S. PATENT DOCUMENTS 5,537,452 A * 7/1996 Shepherd ............... A61N 5/103
378/65
2003/0053075 A1* 3/2003 Duhon ................. A61N 5/1049
356/500
2014/0044141 A1 2/2014 Bouliniere

FOREIGN PATENT DOCUMENTS

CN 1778274 A 5/2006
CN 201596258 U 10/2010
(Continued)

*Primary Examiner* — Rex R Holmes
*Assistant Examiner* — Sana Sahand
(74) *Attorney, Agent, or Firm* — Emerson, Thomson & Bennett, LLC; Roger D. Emerson; Warren A. Rosborough

(57) ABSTRACT

The present disclosure discloses a laser verification apparatus employed in a radiotherapeutic device which comprises a plurality of radioactive sources, a collimator comprising a plurality of collimating holes, and a couch. The radioactive sources are capable of aligning in respect to the collimating holes respectively. The laser verification apparatus comprises: a positioning plate, fixed on the multi-source radiotherapy equipment and arranged between the radiation sources and the collimators; a movable plate, arranged on and movable relative to the positioning plate, and provided with a plurality of first mounting holes and a plurality of second mounting holes, which are arranged one by one, alternately, the movable plate is configured to switch the plurality of first mounting holes or the plurality of second mounting holes to positions corresponding to the plurality of collimators; a plurality of laser emitters respectively received in the second mounting holes, and an acquisition
(Continued)

analyzer arranged on the couch and configured to acquire the light beams emitted by the laser emitters and perform data analysis.

18 Claims, 4 Drawing Sheets

(51) Int. Cl.
    *A61N 5/06*     (2006.01)
    *A61N 5/067*     (2006.01)

(52) U.S. Cl.
    CPC ................. *A61N 2005/0626* (2013.01); *A61N 2005/0632* (2013.01); *A61N 2005/1094* (2013.01); *A61N 2005/1095* (2013.01)

(56) References Cited

FOREIGN PATENT DOCUMENTS

| | | |
|---|---|---|
| CN | 202715140 U | 2/2013 |
| CN | 203647890 U | 6/2014 |

* cited by examiner

RADIOTHERAPEUTIC DEVICE AND LASER VERIFICATION APPARATUS THEREOF

TECHNICAL FIELD

The present invention relates to a radiotherapeutic device, and more particularly to a laser verification apparatus and a multi-source radiotherapeutic device for realizing the opening or closing of partial radioactive sources.

BACKGROUND

During radiation therapy, in order to avoid radiation damage to the normal tissue, it is needed to provide very precise positioning for a collimator, an irradiation field and the patient. A laser positioning system is a device commonly used for precision calibration in radiotherapy, which ensures the accuracy and reproducibility of the treatment equipment. The accuracy of the existing treatment equipment is usually assured through calibration of the radiotherapy field and focal point dose, unfortunately, the operation is complicated with longer time and higher cost.

SUMMARY

The present invention provides a laser verification apparatus used in a multi-source radiotherapeutic device, to solve the problems mentioned above.

In one embodiment, a laser verification apparatus is provided in a radiotherapeutic device which at least comprises a plurality of radioactive sources, a plurality of collimators and a couch. The radioactive sources are capable of aligning in respect to the collimators. The laser verification apparatus comprises: a positioning plate, fixed on the radiotherapeutic device and disposed between the radioactive source and the collimator; a movable plate, disposed on the positioning plate and movable to the positioning plate, the movable plate comprising a plurality of first mounting holes and a plurality of second mounting holes, which are alternately arranged one by one, the movable plate is configured to switch the plurality of first mounting holes or the plurality of second mounting holes to positions corresponding to the plurality of collimators; a plurality of laser emitters, respectively received in the second mounting holes; and an acquisition analyzer, disposed on the couch, and configured to acquire light beams emitted by the laser emitters and perform data analysis. Wherein, when said plurality of radioactive sources are closed, the movable plate moves the laser emitters in the second mounting holes to positions corresponding to the collimating holes, so that the light beams emitted by the laser emitter are irradiated onto the acquisition analyzer; when the radioactive sources are opened, the movable plate moves the first mounting holes to positions corresponding to the collimating holes of the collimator, so that the radiation rays emitted from the radioactive source are irradiated onto the target.

The present invention further comprises a radiotherapeutic device includes the laser verification apparatus mentioned above.

The laser verification apparatus employed in the multi-source radiotherapeutic device of the present invention can verify the accuracy of the collimator and the radiation field shape without the presence of a radioactive source or with closed radioactive source, and thereby automatically calibrate the device accuracy. Moreover, the user can visually observe the shape of the radiation field and the accurate position of the radiation field and focal point in the environment without radiation (radioactive source is turned off), so that the accuracy of the radiotherapeutic device can be directly calibrated as needed.

DETAILED DESCRIPTION

The following descriptions are of exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

The First Embodiment

Figure 1:
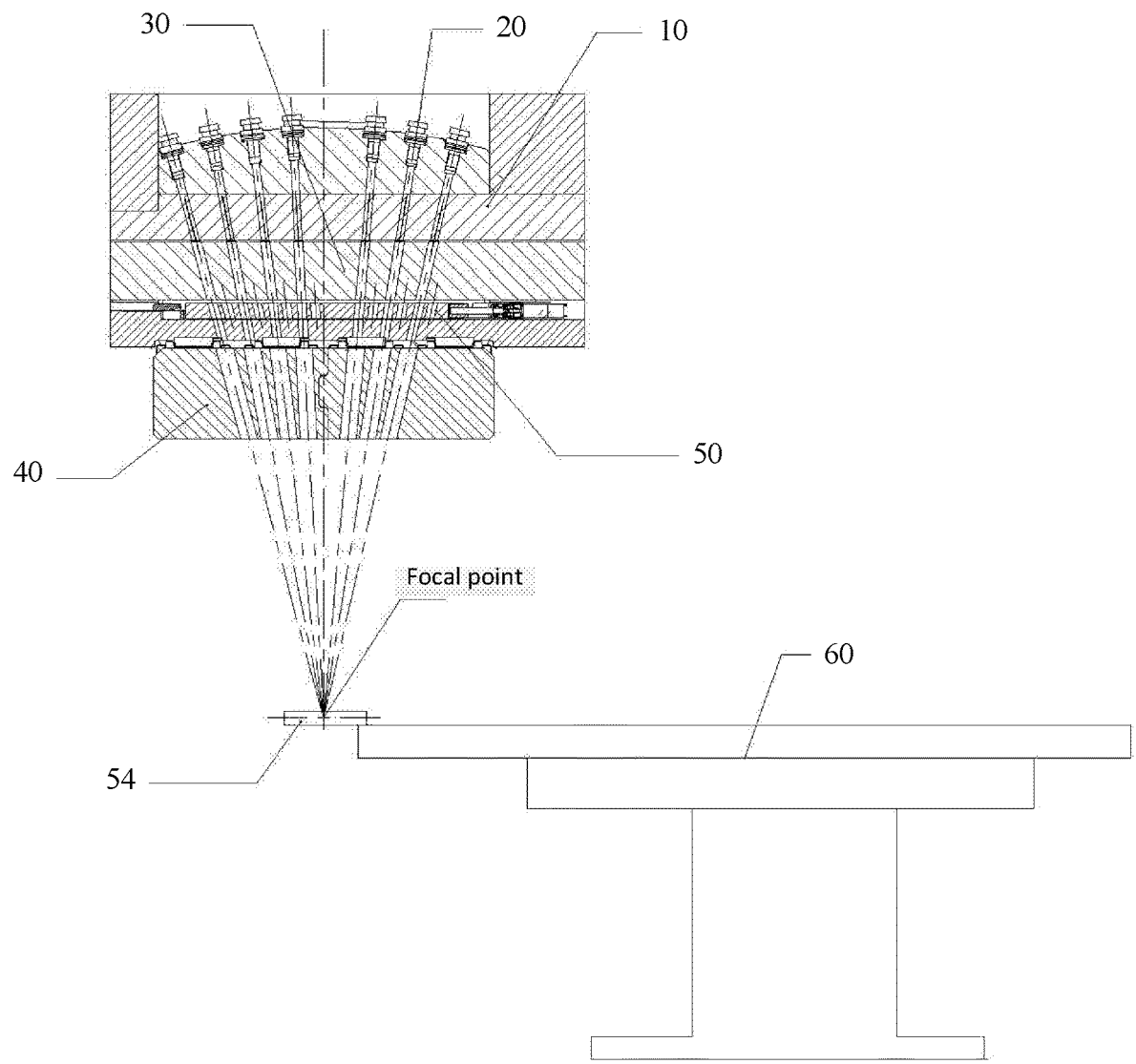
FIG. 1 is a schematic structural view of a multi-source radiotherapeutic device according to a first embodiment of the present invention.

Referring to FIG. 1, which is a schematic structural view of a radiotherapeutic device 100 according to a first embodiment of the present invention. In the present embodiment, the radiotherapeutic device 100 is a multi-source radiotherapeutic device. The radiotherapeutic device 100 includes at least one source carrier 10, a plurality of radioactive sources 20, a pre-collimator 30, a collimator 40, a laser verification apparatus 50, and a couch 60. The plurality of radioactive sources 20 are disposed on the source carrier 10, the laser verification apparatus 50 is disposed between the radioactive sources 20 and the couch 60, the pre-collimator is disposed between the source carrier 10 and the laser verification apparatus 50, and the collimator 40 is disposed between the laser verification apparatus 50 and the couch 60. The pre-collimator 30 includes a plurality of pre-collimated passages, the collimator 40 includes a plurality of collimating holes the plurality of radioactive sources 20 are aligned in respect to the pre-collimated passages of the pre-collimator 30 and the collimating holes of the collimator 40, respectively.

In the present embodiment, the source carrier 10 is bowl-shaped and rotatable relative to the collimator 40 so that the radioactive sources 20 can be moveable relative to the collimator 40. In other embodiments, it will be appreciated that the source carrier 10 may also be annular or arcuate and that the radioactive sources 20 may also be configured to remain stationary relative to the collimator 40. The source carrier 10 is provided with a plurality of radiation holes for respectively receiving the radioactive sources 20. The radiation beams from the radioactive sources 20 are focal pointed through the radiation holes in an open state.

The pre-collimator 30 is provided with a plurality of pre-collimated passages corresponding to the radioactive sources 20, to effect a ray-limiting function to shield unwanted rays away, and to pass through expected rays from the pre-collimated passages to be focal pointed on a focal point.

Figure 2:
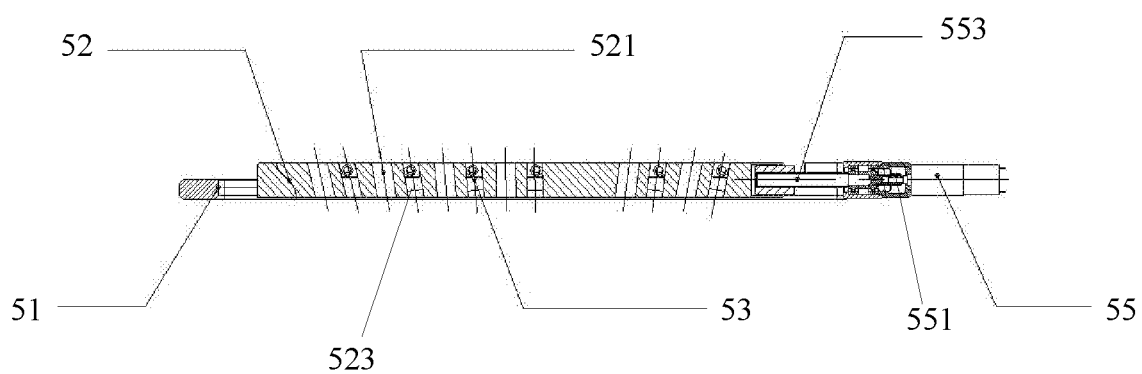
FIG. 2 is a partial structural view of a laser verification apparatus used in the multi-source radiotherapeutic device of FIG. 1.
Figure 3:
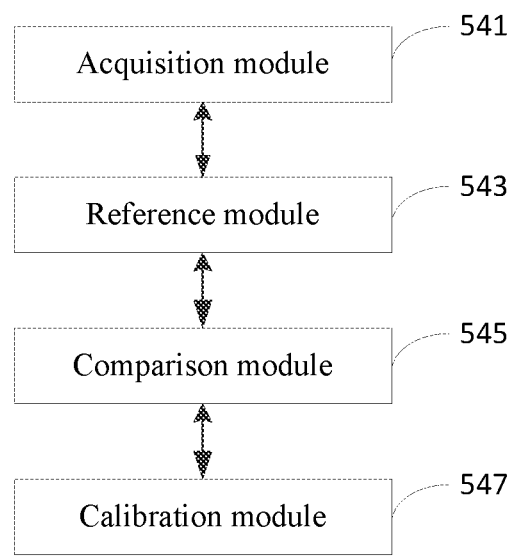
FIG. 3 is a functional block diagram of an acquisition analyzer of the laser verification apparatus of FIG. 2.

Referring FIG. 2, the laser verification apparatus 50 includes a positioning plate 51, a movable plate 52, a plurality of laser emitters 53, and an acquisition analyzer 54 which is shown in FIGS. 1 and 3 but omitted in FIG. 2. The positioning plate 51 is fixed to a mounting bracket (not shown) of the radiotherapeutic device 100 and is disposed on the collimator 40. The movable plate 52 is disposed on the positioning plate 51, and the laser emitters 53 are disposed on the movable plate 52, and the acquisition analyzer 54 is provided on the couch 60.

Referring FIG. 2, the laser verification apparatus 50 includes a positioning plate 51, a movable plate 52, a plurality of laser emitters 53, and an acquisition analyzer 54. The positioning plate 51 is fixed to a mounting bracket (not shown) of the radiotherapeutic device 100 and is disposed on the collimator 40. The movable plate 52 is disposed on the positioning plate 51, and the laser emitters 53 are disposed on the movable plate 52, and the acquisition analyzer 54 is provided on the couch 60.

More specifically, the positioning plate 51 has a straight plate shape, and is provided with a sliding groove (not shown). In other embodiments, the shape of the positioning plate 51 may be provided in the same shape as the source carrier 10.

The movable plate 52 is disposed in the sliding groove of the positioning plate 51 and is movable along the sliding groove with respect to the positioning plate 51. Specifically, the movable plate 52 is connected to the positioning plate 51 through a driving apparatus 55. The driving apparatus 55 includes a drive portion 551 fixed to the positioning plate 51 and a transmission portion 553 connected to one end of the movable plate 52. The movable plate 52 is movable in the sliding groove with respect to the positioning plate 51 in following the transmission portion 553, which is driven by the drive portion 551. The movable plate 52 is provided with a plurality of first mounting holes 521 and a plurality of second mounting holes 523, which are arranged one by one, alternately. The movable plate 52 is configured to switch the plurality of first mounting holes 521 or the plurality of second mounting holes 523 to positions corresponding to the plurality of collimators 40. In the present embodiment, the number of the first mounting holes 521 and the second mounting holes 523 is an even number, and the first mounting holes 521 are symmetrically distributed on both sides of the center line of the movable plate 52, and the second mounting holes 523 are also symmetrically distributed on both sides of the center line of the movable plate 52. A central axis of each first mounting hole 521 and that of the second mounting hole 523 are formed with a specific inclination angle with respect to the center line of the movable plate 52, so that extension lines of the central lines of the first mounting holes 521 can pass through the focal point, and extension lines of the central lines of the plurality of the second mounting holes 523 can also pass through the focal point. Wherein, the focal point is disposed on the acquisition analyzer 54. In the present embodiment, the plurality of first mounting holes 521 and the plurality of second mounting holes 523 are through holes, and the number of the first mounting holes 521 is equal to that of the second mounting holes 523. A distance between the adjacent first mounting hole 521 and the second mounting hole 523 is equal. When the driving apparatus 55 drives the movable plate 52 to move, the plurality of the first mounting holes 521 and the plurality of the second mounting holes 523 are alternately aligned with the radiation holes of the source carrier 10 and the collimating holes of the collimator 40.

The plurality of laser emitters 53 are disposed in the plurality of second mounting holes 523, respectively. In the present embodiment, the laser emitter 53 emits visible light. It will be appreciated that in other embodiments, the visible light may also be transmitted by other types of emitters, which is not limited to laser emitters 53.

When in treatment, the plurality of radioactive sources 20 are opened, and the movable plate 52 moves the plurality of first mounting holes 521 to positions corresponding to the collimating holes of the collimator 40, so that the radiation rays emitted from the radioactive source 20 are irradiated onto the couch 60, that is, the position where the focal point is located. And, when the position detection is required, the plurality of radioactive sources 20 are closed, and the movable plate 52 moves the laser emitter 53 in the plurality of second mounting holes 523 to be in correspondence to collimating holes of the collimator 40, so that the light beams emitted by the laser emitter 53 are irradiated onto the acquisition analyzer 54.

The acquisition analyzer 54 is configured to acquire the light beams emitted by the laser emitters 53 and perform data analysis according to user's needs. In particular, when the couch 60 is moved to a corresponding treatment location and the acquisition analyzer 54 is located at the focal point of the light beams emitted by the laser emitter 53, the acquisition analyzer 54 is capable of acquiring various parameters of the emitted beams from the laser emitter 53, such as a spot shape of the beam, a spot size, a spot position, intensity of the light beam, and so on. In the present embodiment, the acquisition analyzer 54 integrates a microprocessor, which can directly analyze and calculate the data acquired by the acquisition analyzer 54 and send a calibration signal directly to the source carrier 10, the pre-collimator 30, the collimator 40, and the couch 60 to calibrate them. Of course, the setting of the acquisition analyzer 54 is not limited thereto. In other embodiments, the acquisition analyzer 54 is connected to a computer for controlling devices, and the acquisition analyzer 54 can only perform spot acquisition and data analysis and then sends the data analysis results to the computer for post-calculation processing.

Referring now to FIG. 3, more specifically, the acquisition analyzer 54 includes an acquisition module 541, a reference module 543, a comparison module 545, and a calibration module 547.

The acquisition module 541 is configured to acquire the light beams emitted by the laser emitters 53 and obtain relevant parameters such as spot shapes of light beams, spot sizes, spot positions, intensities, and the like. In the present embodiment, the acquisition module 541 uses the technique of contour recognition to obtain parameters for the spot shape and the spot size.

The reference module 543 restores a plurality of original reference data. In the present embodiment, the original reference data in the reference module 543 is obtained by measuring the relevant parameters of the laser verification apparatus 50 after mechanically calibrates the multi-source radiotherapeutic device. Specifically, after calibrating the accuracy of the multi-source radiotherapeutic device 100 by tooling, the radiotherapeutic device 100 is in a state where the radioactive sources 20 are closed. The laser emitter 53 of the laser verification apparatus 50 is moved to a position corresponding to the collimating hole of the collimator 40, the laser emitter 53 is energized to generate a laser beam, and the laser beam is emitted through the collimating hole.

The couch 60 deliveries the laser acquisition analyzer 54 to the focal position and performs data acquisition (spot size, intensity, position, etc.). The data acquired by the laser acquisition analyzer 54 and the current position coordinate data of the couch 60 are input to the microprocessor of the laser verification apparatus 50 as the original reference data of the laser verification apparatus 50. In other embodiments, in order to improve the accuracy of the original reference data, the original reference data may also be set as an average of the results from multiple verifications.

The comparison module 545 is configured to compare the data currently acquired by the acquisition module 541 with the original reference data in the reference module 543. In the present embodiment, the comparison module 545 acquires the comparison results between the currently acquired data with the original reference data in the reference module 543, by establishing a coordinate system and identifying/marking the currently acquired data and the original reference data in the coordinate system, respectively, and then comparing the coordinate points.

The calibration module 547 is configured to calculate a calibration value based on the comparison result from the comparison module 545, and to feed the calibration value back to the collimator 40 and the couch 60 to calibrate the collimator 40 and the couch 60 to meet the criteria.

When the device accuracy calibration is required, the radiotherapeutic device 100 is in a closed state of the radioactive source 20, the laser acquisition analyzer 54 is placed at a specific location of the couch 60, and the position accuracy check button is activated. The couch 60 drives the laser acquisition analyzer 54 to move along a trace which coordinate values are recorded in the laser verification apparatus 50. The collimator 40 are located at the collimating holes for acquisition of original reference data, the movable plate 52 moves the laser emitters 53 to position corresponding to the collimating holes of the collimator 40, and the laser emitters 53 are energized to emit laser beams. The laser acquisition analyzer 54 performs data acquisition and analysis. The laser verification apparatus 50 compares the currently acquired data with the original reference data (spot size, intensity, position, etc.) to calculate the deviation value and supplies it to the control device of the collimator 40 and the couch 60, so that the control device can calibrate the position of the equipment according to the deviation data, to ensure accuracy of the equipment.

The Second Embodiment

Figure 4:
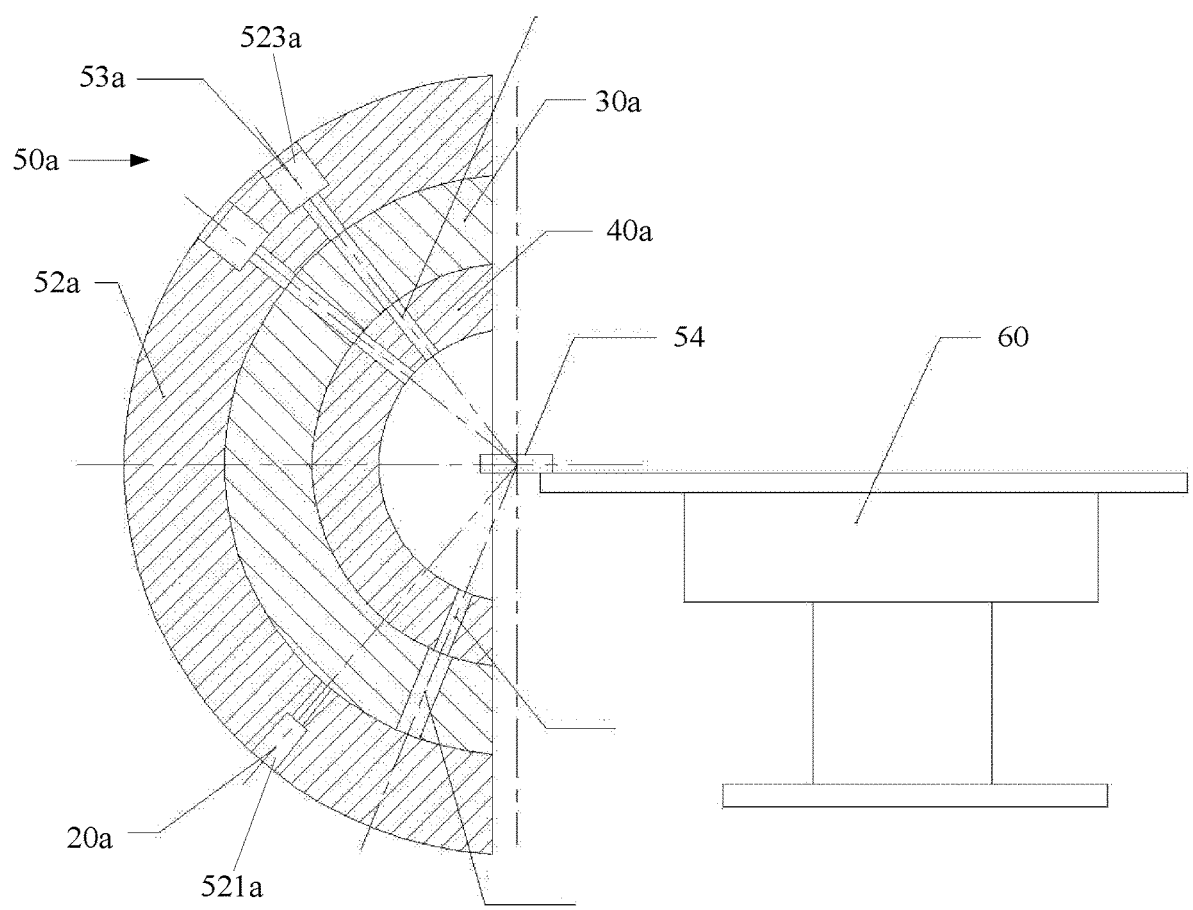
FIG. 4 is a schematic structural view of a multi-source radiotherapeutic device according to a second embodiment of the present invention.

Referring to FIG. 4, the multi-source radiotherapeutic device 200 of the second embodiment of the present invention is substantially the same as the multi-source radiotherapeutic device 100 of the first embodiment, with the difference that while the plurality of laser emitters 53a are received in the second mounting holes 523a of the movable plate 52a, the plurality of radioactive sources 20a are received in the first mounting holes 521a of the movable plate 52a, respectively. That is, the movable plate 52a of the laser verification apparatus 50a replaces the rotatable source carrier 10 in the first embodiment, so that the radioactive source 20a and the laser emitter 53a are simultaneously disposed on the movable plate 52a. At this time, the pre-collimator 30a is disposed between the movable plate 52a of the laser verification apparatus 50a and the collimator 40a. As a result, the volume and cost of the radiotherapeutic device 200 are saved.

The laser verification apparatus employed in the multi-source radiotherapeutic device of the present invention can verify the accuracy of the collimator and the radiation field shape without the presence of a radioactive source or with closed radioactive source, and thereby automatically calibrate the device accuracy. Moreover, the user can visually observe the shape of the radiation field and the accurate position of the radiation field and focal point in the environment without radiation (radioactive source is turned off), so that the accuracy of the radiotherapeutic device can be directly calibrated as needed.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

What is claimed is:

1. A laser verification apparatus, employed in a radiotherapeutic device which at least comprises a plurality of radioactive sources, a collimator comprising a plurality of collimating holes, and a couch, the radioactive sources being capable of aligning in respect to the collimating holes, wherein the laser verification apparatus comprises:

a movable plate, comprising a plurality of first mounting holes and a plurality of second mounting holes, the first mounting holes and second mounting holes being spaced apart in the movable plate, the movable plate being configured to switch the plurality of first mounting holes or the plurality of second mounting holes to positions corresponding to the plurality of collimating holes;

a plurality of laser emitters respectively disposed in the second mounting holes; and an acquisition analyzer configured to acquire light beams emitted by the laser emitters and perform data analysis, wherein when said plurality of radioactive sources are closed, the movable plate is configured to move the laser emitters in the second mounting holes to first positions corresponding to the collimating holes such that the light beams emitted by the laser emitter are irradiated onto the acquisition analyzer; when the radioactive sources are opened, the movable plate is configured to move the first mounting holes to second positions corresponding to the collimating holes of the collimator such that the radiation rays emitted from the radioactive sources are irradiated onto a target area.

2. The laser verification apparatus of claim 1, wherein the plurality of radioactive sources are disposed above the movable plate, or the plurality of radioactive sources are disposed in the first mounting holes of the movable plate.

3. The laser verification apparatus of claim 1, further comprising a positioning plate disposed between the radioactive sources and the collimator, and the laser verification apparatus further comprises a driving apparatus which comprises a drive portion fixed to the positioning plate and a transmission portion connected to the movable plate, wherein, driven by the drive portion, the movable plate is movable relative to the positioning plate.

4. The laser verification apparatus of claim 1, wherein a central line of each first mounting hole and that of the second mounting hole are formed with a specific inclination angle with respect to a center line of the movable plate, so that extension lines of the central lines of the first mounting holes passes through a focal point, and extension lines of central lines of the plurality of the second mounting holes also passes through the focal point.

5. The laser verification apparatus of claim 1, wherein said acquisition analyzer comprises:
- an acquisition module configured for acquiring the light beams emitted by the laser emitters and obtaining the relevant parameters;
- a reference module configured for restoring a plurality of original reference data;
- a comparison module configured for comparing currently acquired data from the acquisition module with the original reference data in the reference module; and
- a calibration module configured for calculating a calibration value based on a comparison result of the comparison module and feeding the calibration value back to the collimator and the couch to calibrate the collimator and the couch.

6. The laser verification apparatus of claim 5, wherein the relevant parameters comprises spot size, light intensity, and spot position.

7. The laser verification apparatus of claim 5, wherein the original reference data in the reference module is an average value with multiple calibrations.

8. The laser verification apparatus of claim 5, wherein the original reference data in the reference module is obtained by measuring the relevant parameters of the laser verification apparatus after the radiotherapeutic device is calibrated.

9. The laser verification apparatus of claim 3, wherein the positioning plate is fixed to the radiotherapeutic device and is disposed on the collimator, the movable plate is disposed on the positioning plate, the laser emitters are disposed on the movable plate, and the acquisition analyzer is provided on the couch.

10. The laser verification apparatus of claim 3, wherein the radiotherapeutic device includes at least one source carrier, and the positioning plate and the source carrier are of the same shape.

11. The laser verification apparatus of claim 3, wherein the positioning plate is provided with at least one sliding groove, the movable plate is disposed in the sliding groove of the positioning plate and is movable along the sliding groove with respect to the positioning plate.

12. The laser verification apparatus of claim 3, wherein the driving apparatus comprises a drive portion fixed to the positioning plate and a transmission portion connected to one end of the movable plate.

13. The laser verification apparatus of claim 1, wherein a number of the first mounting holes and the second mounting holes is an even number.

14. The laser verification apparatus of claim 1, wherein the first mounting holes are symmetrically distributed on both sides of a center line of the movable plate, and the second mounting holes are also symmetrically distributed on both sides of the center line of the movable plate.

15. The laser verification apparatus of claim 1, wherein the adjacent first mounting holes and second mounting holes are spaced apart with a same interval.

16. The laser verification apparatus of claim 5, wherein the comparison module further establishes a coordinate system and identifies/marks the currently acquired data and the original reference data in the coordinate system, respectively, and then comparing the coordinate points.

17. The radiotherapeutic device of claim 7, wherein said acquisition analyzer comprises:
- an acquisition module configured for acquiring the light beams emitted by the laser emitters and obtaining the relevant parameters;
- a reference module configured for restoring a plurality of original reference data;
- a comparison module configured for comparing the currently acquired data from the acquisition module with the original reference data in the reference module; and
- a calibration module configured for calculating a calibration value based on a comparison result of the comparison module and feeding the calibration value back to the collimator and the couch to calibrate the collimator and the couch.

18. A radiotherapeutic device comprising a plurality of radioactive sources, a collimator, a couch, and a laser verification apparatus, the radioactive sources being capable of aligning in respect to collimating holes of the collimator, the laser verification apparatus being positioned between the plurality of radioactive sources and the couch, wherein the laser verification apparatus comprises:
- a movable plate, comprising a plurality of first mounting holes and a plurality of second mounting holes, the first mounting holes and second mounting holes being spaced apart in the movable plate, the movable plate being configured to switch the plurality of first mounting holes or the plurality of second mounting holes to positions corresponding to the plurality of collimating holes;
- a plurality of laser emitters respectively received in the second mounting holes; and
- an acquisition analyzer configured to acquire light beams emitted by the laser emitters and perform data analysis,
    - wherein when said plurality of radioactive sources are closed, the movable plate is configured to move the laser emitters in the second mounting holes to first positions corresponding to the collimating holes such that the light beams emitted by the laser emitter are irradiated onto the acquisition analyzer; when the radioactive sources are opened, the movable plate is configured to move the first mounting holes to second positions corresponding to the collimating holes of the collimator such that the radiation rays emitted from the radioactive sources are irradiated onto a position of a focal point.

* * * * *